US00PP31857P3

(12) United States Plant Patent
Suphachadiwong

(10) Patent No.: US PP31,857 P3
(45) Date of Patent: Jun. 9, 2020

(54) ***VANDA* PLANT NAMED 'SPCDW1812'**

(50) Latin Name: ***Vanda* spp. Jones ex R. Br.**
Varietal Denomination: SPCDW1812

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 16/501,500

(22) Filed: Apr. 18, 2019

(65) Prior Publication Data

US 2019/0327875 P1 Oct. 24, 2019

(30) Foreign Application Priority Data

Apr. 18, 2018 (QZ) ..... PBR 2018/1081

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

*Primary Examiner* — Susan McCormick Ewoldt
(74) *Attorney, Agent, or Firm* — Samuel R. McCoy, Jr.

(57) ABSTRACT

A new and distinct *Vanda* plant named 'SPCDW1812' which is characterized by a freely flowering bloom habit, nearly pure white flowers, moderately ruffled petals and sepals, lateral petals which are axially twisted to horizontal, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1812'.

CROSS REFERENCE TO RELATED APPLICATIONS

This application claims priority to the Community Plant Variety Rights application number 2018/1081, filed Apr. 18, 2018, which is herein incorporated by reference.

BACKGROUND OF THE INVENTION

Parentage: The new *Vanda* plant, 'SPCDW1812', originated as a naturally-occurring whole plant mutation of *Vanda* 'SPCDW0901' (U.S. Plant Pat. No. 23,344). In November of 2010, the inventor discovered the mutation at a commercial greenhouse in Bangphra, Thailand growing amongst a cultivated population of *Vanda* 'SPCDW0901'. The mutation was noted for its solid white flowers and was subsequently isolated for further evaluation in order to confirm the distinctness and stability of the characteristics first observed. Upon confirmation of distinctness and stability, 'SPCDW1812' was selected for commercialization.

Asexual Reproduction: Asexual reproduction of the new cultivar 'SPCDW1812', by way of mericloning, was first initiated in June of 2011 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1812' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1812'. These characteristics in combination distinguish 'SPCDW1812' as a new and distinct *Vanda* cultivar:

1. *Vanda* 'SPCDW1812' exhibits a freely flowering bloom habit, with large flowers carried above the foliage; and
2. *Vanda* 'SPCDW1812' exhibits petals and sepals that are nearly pure white at anthesis; and
3. *Vanda* 'SPCDW1812' exhibits petals and sepals margins which are moderately undulated; and
4. *Vanda* 'SPCDW1812' exhibits lateral petals which are axially twisted to a horizontal orientation; and
5. *Vanda* 'SPCDW1812' exhibits a white labellum.

BOTANICAL DESCRIPTION OF THE PLANT

Figure 1:
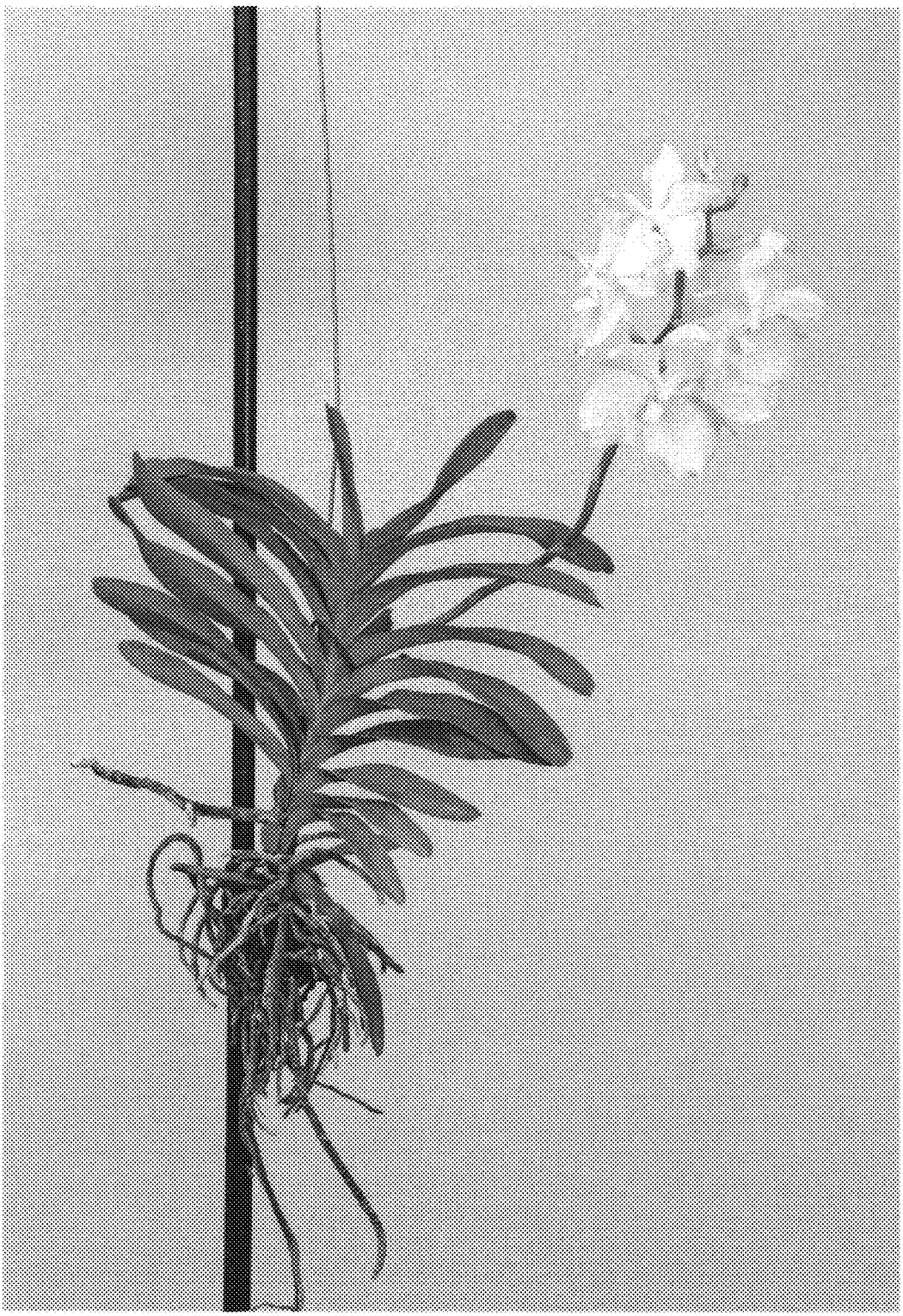
FIG. 1 illustrates, as nearly true as it is reasonably possible to make the same in color photographs of this type, an exemplary plant of 'SPCDW1812' grown in a commercial greenhouse in Honselersdijk, the Netherlands. This plant is approximately 6 years old from the time of mericloning, shown planted in an 8 by 2 cm container.
Figure 2:
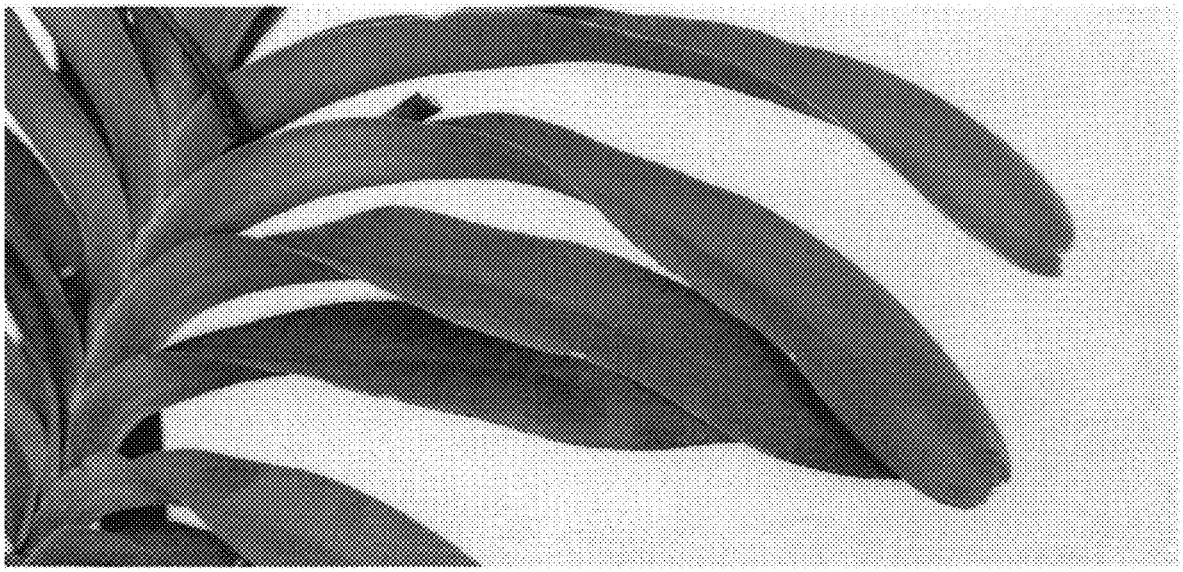
FIG. 2 illustrates, as nearly true as it is reasonably possible to make the same in color photographs of this type, the typical foliage of 'SPCDW1812'.
Figure 3:
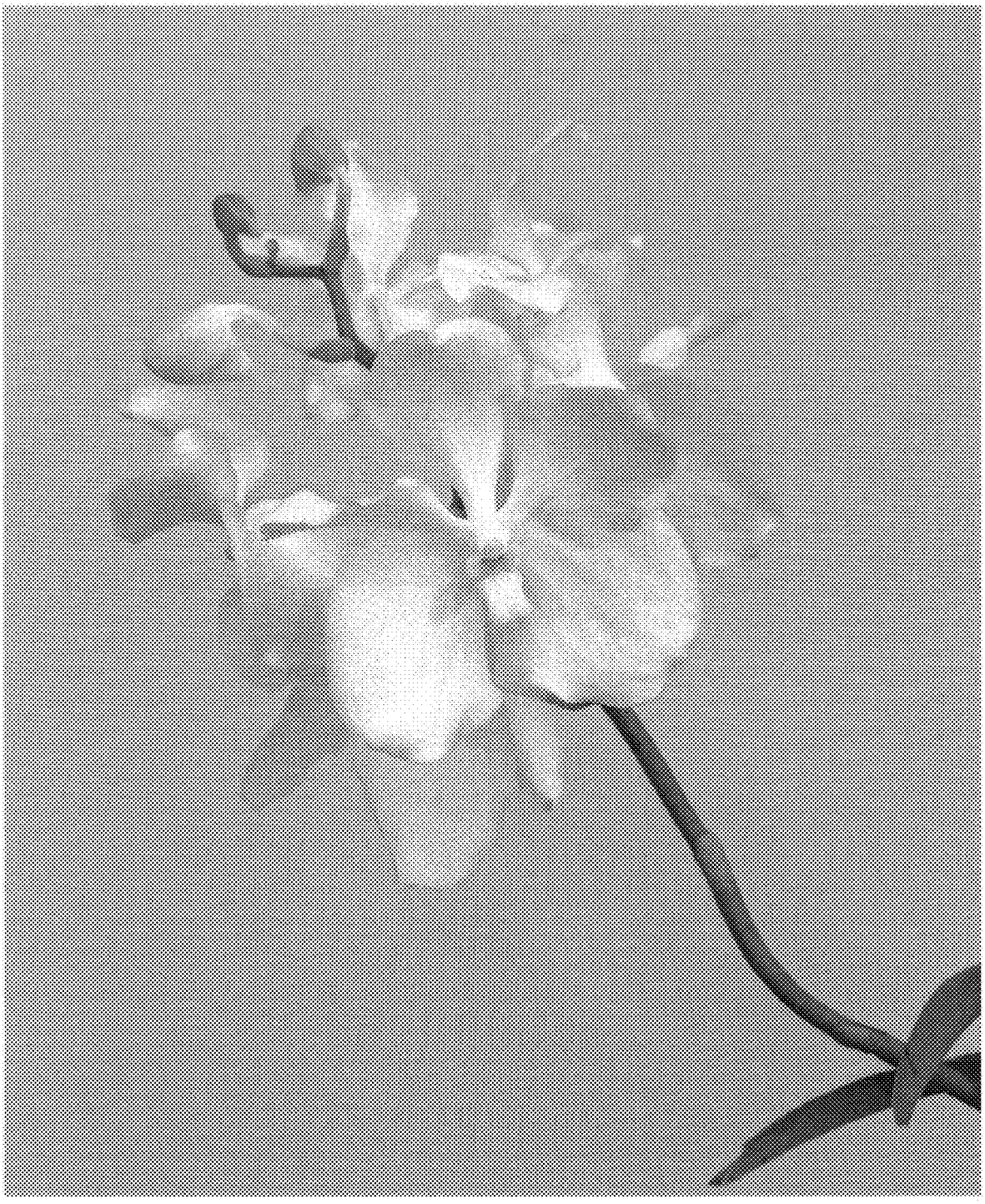
FIG. 3 illustrates, as nearly true as it is reasonably possible to make the same in color photographs of this type, the typical inflorescence of 'SPCDW1812'.
Figure 4:
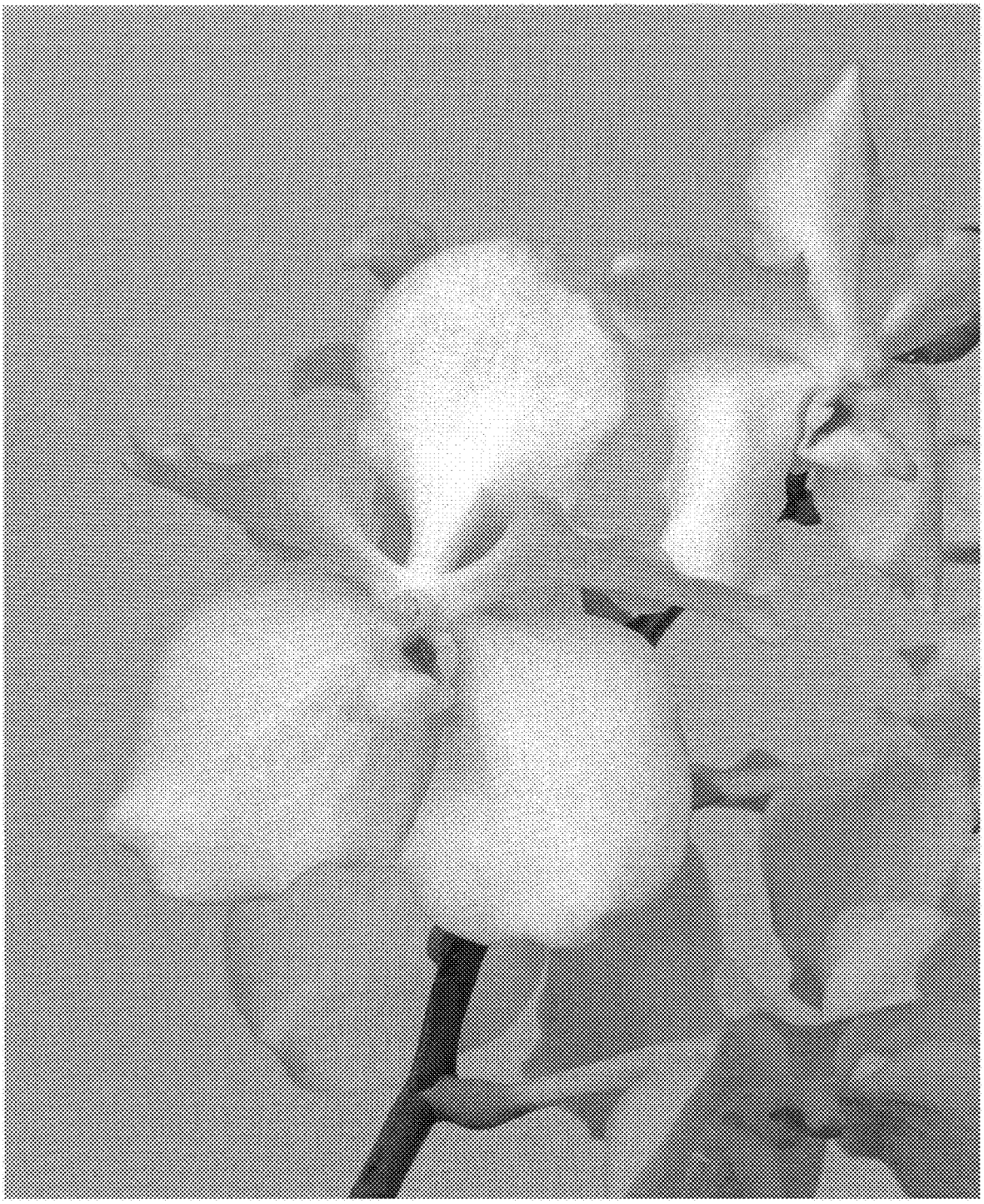
FIG. 4 illustrates, as nearly true as it is reasonably possible to make the same in color photographs of this type, the typical flower of 'SPCDW1812'.

The following observations and measurements made in March of 2019 describe averages from a sample set of six specimens of six year-old 'SPCDW1812' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1812' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1812' and comparisons with the parent and most similar commercial variety of *Vanda* are provided below.

Plant description:

*Growth habit*.—Perennial; monopodial, upright. Single monopodial leafy stem, with flowers carried above the leaf plane; inflorescences growing from the leaf axils.

*Average height from base (plant grown in hanging basket, so no soil line present) to foliar plane*.—37.8 cm.

*Average height from base (plant grown in hanging basket, so no soil line present) to top of floral plane*.—55.5 cm.

*Plant spread*.—Average of 39.5 cm.

*Appropriate container size*.—8 cm by 2 cm rectangular hanging basket.

*Growth rate*.—Moderate.

*Plant vigor*.—Moderate.

*Propagation type*.—Meristematic tissue culture propagation using the base of the leaves.

*Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility*.—Plants have not been observed to be susceptible or resistant to pathogens and pests common to *Vanda*.

*Environmental tolerances*.—Adapt to, at least, USDA Zones 11 and 12 and temperatures as high as 40 degrees Celsius; high tolerance to rain; moderate to high tolerance to wind.

Root system:

*General*.—Moderately to densely rooting; with aerial roots only.

*Dimensions, mature roots*.—19.0 cm long with a diameter of 0.6 cm, on average.

*Texture*.—Very fleshy; non-fibrous.

*Color*.—Greyed-green, nearest to RHS 192D; root apex is yellow-green, RHS 148A.

Stem:

*Branching habit*.—Monopodial; no lateral branches present.

*Number of primary (main) stems per plant*.—One.

*Number of secondary (lateral) branches per plant*.—None.

*Aspect*.—Circular, formed by the leaf sheaths.

*Length*.—22.0 cm.

*Diameter*.—0.8 cm.

*Internode length*.—0.9 cm.

*Pubescence*.—Glabrous.

*Luster*.—Matte.

*Attitude, main stem*.—Near vertical.

*Strength*.—Very strong.

*Color, juvenile*.—Yellow-green, nearest to RHS 145D.

*Color, mature*.—Yellow-green, nearest to RHS 145D.

*Color at internodes*.—Yellow-green, nearest to RHS 145D.

Foliage:

*Arrangement*.—Distichous.

*Dimensions*.—20.4 cm long, excluding the sheath, and 2.8 cm wide.

*Shape of blade*.—Ligulate.

*Aspect*.—Moderately carinate; axially twisted and strongly curled inward.

*Attitude*.—Slightly curled downward.

*Apex*.—Unequal praemorse.

*Base*.—Sheathing.

*Sheath dimensions*.—3.5 cm long and 1.0 cm wide, on average.

*Sheath color*.—Yellow-green, nearest to RHS 144C.

*Margin*.—Entire.

*Pubescence, texture and luster of adaxial surface*.—Glabrous, smooth, and matte.

*Pubescence, texture and luster of abaxial surface*.—Glabrous, smooth, and matte.

*Color*.—Juvenile foliage, adaxial surface — Nearest to in between green and yellow-green, RHS 143A and 144A, and becoming green towards the margins and apex, nearest to RHS 137B. Juvenile foliage, abaxial surface — Yellow-green, nearest to RHS 144A. Mature foliage, adaxial surface — Green, nearest to RHS 137B. Mature foliage, abaxial surface — Yellow-green, nearest to in between RHS 144A and 146B, and becoming green towards the margins and apex, nearest to RHS 143A.

*Venation*.—Pattern — Parallel. Color, adaxial surface — Green, nearest to RHS NN137C. Color, abaxial surface — Green, nearest to a mixture of RHS 143B and 143C.

*Petiole*.—No petioles present; leaves sessile.

Inflorescence:

*Inflorescence arrangement*.—Axially placed raceme.

*Natural flowering season*.—Autumn into winter.

*Time to flower*.—Approximately 10 months.

*Flowers per inflorescence*.—Average of 9.

*Flowers per plant*.—6 open flowers and 3 flower buds.

*Inflorescence height*.—Approximately 20.5 cm (measured from base of lowest flower to top of upper flower).

*Inflorescence diameter*.—Approximately 17.4 cm.

*Peduncle*.—Dimensions — Approximately 41.5 cm long and 0.7 cm wide. Attitude — Generally at a 45 degree angle to lateral branch axis. Strength — Moderately strong. Texture and luster — Glabrous and matte. Color — Green, nearest to a mixture of RHS 143B and 143C.

Bud:

*Length*.—Average of 1.5 cm.

*Diameter*.—Average horizontal diameter is 1.4 cm; the vertical diameter is 2.2 cm.

*Shape*.—Broad obovate to near globular, with a deltoid apex which is pointed downward.

*Pubescence, texture and luster*.—Glabrous, smooth and slightly glossy.

*Color*.—Yellow-green, nearest to RHS 145C, and fading to green-white towards the apex, nearest to RHS 157D.

Flower:

*Flower type*.—Zygomorphic (orchidaceous), typical shape for the genus *Vanda*.

*Flowering habit*.—Moderately free flowering.

*Shape*.—Zygomorphic, single; consisting of three sepals and three petals, one of which is transformed into a labellum; the lateral petals are axially twisted to near horizontal and do not overlap the lateral sepal and dorsal sepals; lateral sepals touch one another.

*Attitude*.—Flowers are outward-facing.

*Vertical height*.—Approximately 10.6 cm.

*Diameter*.—Approximately 10.3 cm.

*Depth*.—Approximately 4.9 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 5.3 cm. Width — Approximately 4.3 cm. Shape — Broad ovate. Apex — Obtuse to shallow emarginate. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — White, nearest to RHS 155C. Color when opening, lower surface — White, nearest to RHS 155C. Color when fully opened, upper surface — White, nearest to RHS NN155D. Color when fully opened, lower surface — White, nearest to RHS NN155D. Fading, upper surface — Not fading. Fading, lower surface — Not fading. Venation color, fully opened, upper surface — White, nearest to RHS NN155D. Venation color, fully opened, lower surface — White, nearest to RHS NN155D.

*Labellum*.—Shape — Three-lobed; the lateral lobes are obovate and involute; the central lobe is broad obovate to oblong and strongly revolute. Length — Central lobe — Approximately 1.9 cm. Lateral lobes — Approximately 0.6 cm. Width — Central lobe — Approximately 1.2 cm at the base; 1.1 at the apex. Lateral lobes — Approximately 0.7 cm. Apex — Central lobe — Emarginate. Lateral lobes — Emarginate. Base — Central lobe — Broad cuneate. Lateral lobes — Broad cuneate. Margin — Central lobe — Entire; very slightly undulated. Lateral lobes — Entire; not undulated. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — White, nearest to RHS NN155C, and lightly striped yellow at the base, nearest to a mixture of RHS 11C and 11D. Lateral lobes — White, nearest to RHS 155C; base is yellow-orange, nearest to RHS 17C. Color when opening, lower surface — Central lobe — White, nearest to a mixture of RHS NN155B and NN155C. Lateral lobes — White, nearest to RHS NN155C. Color when fully opened, upper surface — Central lobe — White, nearest to RHS NN155C, and fading towards the apex, nearest to RHS N155B. Lateral lobes — White, nearest to RHS 155C; base is yellow-orange, nearest to a mixture of RHS 17C and 17D. Color when fully opened, lower surface — Central lobe — White, nearest to RHS NN155C, and fading towards the apex, nearest to RHS N155B. Lateral lobes — White, nearest to RHS 155C; base is yellow-orange, nearest to a mixture of RHS 17C and 17D. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities*.—Dimensions — 1.5 cm long and 0.8 cm wide, on average. Color — White, nearest to RHS NN155C, and fading towards the apex, nearest to RHS N155B.

*Spurs*.—Quantity — Average of 1. Length — Approximately 0.9 cm. Diameter — Approximately 0.3 cm. Vertical height — Approximately 0.7 cm, at the base. Shape — Short triangular; flattened. Apex — Bluntly acute. Base — Broad cuneate. Pubescence, texture and luster — Glabrous, smooth, and matte. Color — White, nearest to RHS NN155C, and fading towards the apex, nearest to RHS N155B.

*Sepals*.—Quantity — Average of 3 unfused sepals. Arrangement — One dorsal sepal and two lateral sepals. Length — Dorsal sepal — Approximately 6.1 cm. Lateral sepals — Approximately 6.1 cm. Width — Dorsal sepal — Approximately 6.1 cm. Lateral sepals — Approximately 7.0 cm. Shape — Dorsal sepal — Near orbicular. Lateral sepals — Reniform. Apex — Dorsal sepal — Obtuse. Lateral sepals — Obtuse. Base — Dorsal sepal — Cuneate. Lateral sepals — Cuneate. Margin — Dorsal sepal — Entire; moderately undulated. Lateral sepals — Entire; moderately undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — White, nearest to RHS 155C. Lateral sepals — White, nearest to a mixture of RHS NN155A and NN155B, and fading to green-white towards the apex, nearest to RHS 157D. Color when opening, lower surface — Dorsal sepal — Nearest to in between white and green-white, RHS 155C and 157D. Lateral sepals — White, nearest to a mixture of RHS NN155A and NN155B, and fading to green-white towards the apex, nearest to RHS 157C. Color when fully opened, upper surface — Dorsal sepal — White, nearest to RHS NN155C. Lateral sepals — White, nearest to RHS NN155C. Color when fully opened, lower surface — Dorsal sepal — White, nearest to RHS NN155C. Lateral sepals — White, nearest to RHS NN155C. Fading, upper surface — Not fading. Fading, lower surface — Not fading. Venation color, fully opened, upper surface — Dorsal sepal — White, nearest to RHS NN155C. Lateral sepals — White, nearest to RHS NN155C. Venation color, fully opened, lower surface — Dorsal sepal — White, nearest to RHS NN155C. Lateral sepals — White, nearest to RHS NN155C.

*Pedicels*.—Length — Approximately 6.0 cm. Diameter — Approximately 0. 5 cm. Attitude — Approximately 65 degree angle to peduncle axis. Strength — Moderately strong. Texture — Glabrous, axially angled with 5 "ribs", axially twisted (due to resupination). Luster — Moderately glossy. Color — White, nearest to RHS NN155C, and becoming slightly darker towards the distal end, nearest to RHS NN155A.

*Bract*.—Quantity — One bract present at the base of each pedicel. Shape — Reniform; folded around the base of each pedicel. Dimensions — Average of 1.4 cm long and 1.6 cm wide. Apex — Slightly praemorse. Base — Broad cuneate. Margins — Entire. Color, inner surface — Yellow-green, nearest to RHS 151D. Color, outer surface — Yellow-green, nearest to RHS 151D.

Reproductive organs:

*Column*.—Length — Approximately 0.5 cm. Diameter — Approximately 0.7 cm. Color — White, nearest to RHS NN155A.

*Ovary*.—Position — Inferior. Diameter — Approximately 0.2 cm. Color — Green-white, nearest to RHS 157D.

*Pollinia color*.—Yellow-orange, nearest to RHS 14A.

Seed and fruit: No fruit and seed production has been detected to date.

COMPARISON WITH THE PARENT PLANT

Plants of the new cultivar 'SPCDW1812' differ from the *Vanda* seed parent, 'SPCDW0901' (not patented), by the characteristics described in Table 1.

TABLE 1

| Characteristic | 'SPCDW1812' | 'SPCDW0901' |
|---|---|---|
| Vigor; rate of growth. | Considerably slower than 'SPCDW0901'. | Faster growing than 'SCDW1809'. |
| General coloration of the petals and sepals when fully opened. | Solid white. | White and densely reticulated pink. |

COMPARISON WITH THE MOST SIMILAR *VANDA* CULTIVAR KNOWN TO THE INVENTOR

Plants of the new cultivar 'SPCDW1812' are similar to the cultivar, *Vanda* 'SPCDW1517' (U.S. Plant Pat. No. 30,248). A comparison of 'SPCDW1812' with *Vanda* 'SPCDW1517' is described in Table 2.

TABLE 2

| Characteristic | 'SPCDW1812' | 'SPCDW1517' |
|---|---|---|
| Undulation of petal and sepal margins. | More heavily undulated. | Less undulated. |
| Aspect of lateral petals. | Axially twisted to near horizontal. | Not axially twisted; forward-facing. |
| Size of lateral sepals. | Larger than those of 'SPCDW1517'. | Smaller than 'SPCDW1812'. |

That which is claimed is:

1. A new and distinct variety of *Vanda* plant named 'SPCDW1812', substantially as described and illustrated herein.

* * * * *